US00PP16964P2

(12) United States Plant Patent
Zerr

(10) Patent No.: US PP16,964 P2
(45) Date of Patent: Aug. 8, 2006

(54) POINSETTIA PLANT NAMED 'FISCINNE'

(50) Latin Name: *Euphorbia pulcherrima*
Varietal Denomination: Fiscinne

(75) Inventor: Katharina Zerr, Hohr-Grenzhausen (DE)

(73) Assignee: Florfis AG, Binningen (CH)

( * ) Notice: Subject to any disclaimer, the term of this patent is extended or adjusted under 35 U.S.C. 154(b) by 48 days.

(21) Appl. No.: 11/071,957

(22) Filed: Mar. 4, 2005

(51) Int. Cl.
*A01H 5/00* (2006.01)

(52) U.S. Cl. ..... Plt./303

(58) Field of Classification Search ..... Plt./306, Plt./303

See application file for complete search history.

*Primary Examiner*—Kent Bell
*Assistant Examiner*—Annette H Para
(74) *Attorney, Agent, or Firm*—Jondle & Associates P.C.

(57) ABSTRACT

A Poinsettia cultivar particularly distinguished by its salmon-colored bracts with pink freckles, uniform dark green leaves with distinct pointed lobes, and early flowering response is disclosed.

1 Drawing Sheet

Figure 1:
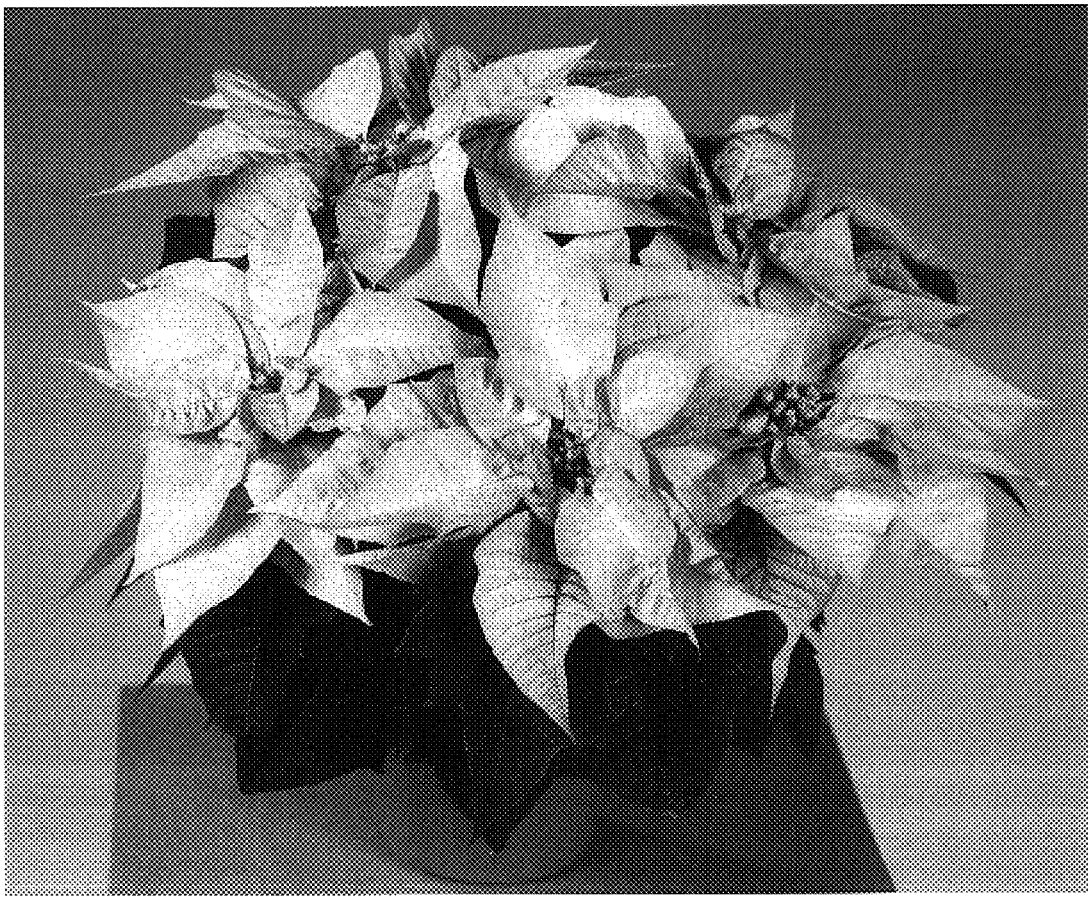

Genus and species: *Euphorbia pulcherrima* (Willd.).
Variety denomination: 'Fiscinne'.

BACKGROUND OF THE NEW PLANT

The present invention relates to a new and distinct cultivar of Poinsettia plant, botanically known as *Euphorbia pulcherrima* (Willd.), and hereinafter referred to by the name 'Fiscinne'. 'Fiscinne' is the result of an induced mutation in the variety 'Fismille' (U.S. Plant Pat. No. 13,660). 'Fismille' is characterized by large, bright red bracts, dark-green foliage, ovate shaped leaves, upright and medium to tall plant habit, and very early flowering time.

Irradiation of young plants of 'Fismille' was conducted in Ahrensburg, Germany on May 1998. The irradiated plants were grown in Hillscheid, Germany and were propagated by cuttings. The flowering plants derived thereof were screened for positive mutations throughout 1999 and later. One plant was selected for propagation by cuttings. The asexually propagated offspring of that plant proved to be uniform when examined in trial cultivations in the fall of 2001 and 2002, and the clone has remained stable since then.

Horticultural examination of the clone starting in 2001 and continuing thereafter has confirmed that the combination of characteristics as herein disclosed for 'Fiscinne' are firmly fixed and retained through successive generations of asexual reproduction.

The following traits have been repeatedly observed and are determined to be the basic characteristics of 'Fiscinne' which in combination distinguish this Poinsettia as a new and distinct cultivar:

- salmon bract color; slightly freckled with pink
- medium to large sized inflorescence, ovate bracts with weak lobes
- uniform dark-green foliage, ovate leaves with distinct, pointed lobes
- medium or over sized, upright plant habit
- early flowering response

DESCRIPTION OF PHOTOGRAPH

This new Poinsettia plant is illustrated by the accompanying photograph which shows the plant's form, foliage and flowers. The colors shown are as true as can be reasonably obtained by conventional photographic procedures.

FIG. 1 shows overall plant habit including foliage and flowers.

DESCRIPTION OF THE NEW CULTIVAR

'Fiscinne' has not been observed under all possible environmental conditions. The phenotype may vary significantly with variations in environment such as temperature, light intensity, and day-length. The following observations, measurements and comparisons describe plants grown in Hillscheid, Germany under greenhouse conditions which approximate those generally used in commercial practice.

The plants described were grown in a greenhouse in Hillscheid, Germany from the summer to the fall of 2004. Rooted cuttings were planted in 14 cm pots on Jul. 22, 2004 and were pinched on August 6, which left 7–8 leaves remaining. Initially, the minimum temperature was 18° C. Beginning October 1, the temperature was lowered to a minimum temperature of 16 to 17° C. The plants initiated flowers under natural short-day conditions in fall. No black cloth was applied to the greenhouse to simulate short-day conditions. No growth regulator was applied.

Observations and measurements were mainly taken in early to mid-December, when the plants were in full flower and about 20 weeks old. In the following description, color references are made to The Royal Horticultural Society Colour Chart (R.H.S.). The color references were determined indoors in a north light.

DESCRIPTION OF THE NEW PLANT

Classification:
*Family.*—Euphorbiaceae.

*Botanical.*—*Euphorbia pulcherrima* (Willd. Ex Klotzsch).

Parentage: Mutation of Poinsettia cultivar 'Fismille' (U.S. Plant Pat. No. 13,660).

Growth:

*Time to produce a rooted cutting.*—20–24 days in a greenhouse at a temperature of 22–24° C.

*Blooming habit.*—Beginning under natural short-day conditions in fall: Botanically (cyathia open): Late November. Commercially (bracts colored, marketable): Mid-November. Flowering response time: About 8 weeks. Keeping quality: Good lasting quality is maintained for about 4–5 weeks with no dropping of bracts.

Plant:

*Form.*—Shrub, self-branching.

*Growth habit.*—About medium or over-sized; pinched plants are bushy, but not very wide, with upward-directed branches and rounded foliage canopy.

*Height.*—29.0 cm as measured from soil line.

*Width.*—42.3 cm.

*Average number of branches.*—5.2.

*Length of branches.*—20–24 cm.

*Diameter of branches.*—0.5–0.6 cm.

*Average number of inflorescences.*—4.5.

Stems:

Stem color:

*Middle part.*—RHS 141A (green).

*Upper part.*—RHS 143A (green) to RHS 143B (green).

*Internode length.*—0.23–0.28 cm.

Leaves:

*Quantity.*—35 leaves per plant (6–7 leaves per branch).

*Shape.*—Ovate to deltoid.

*Base.*—Truncate to weakly obtuse.

*Apex.*—Acuminate.

*Lobes.*—Distinct with pointed tips.

*Margin.*—Entire.

*Texture.*—Upper surface: Smooth and flat, only weakly veined. Lower surface: Flat and smooth, except for the slightly protruding midrib and finer side veins in a pinnate pattern.

*Vein color.*—Upper surface: RHS 144A (green). Lower surface: RHS 144D (green).

*Size.*—Length: 12.0 cm. Width: 10.5 cm.

*Color.*—Mature foliage: Upper surface: RHS 139A. Lower surface: RHS 137B. Immature foliage: Upper surface: RHS 137B. Lower surface: RHS 137D.

*Leaf petiole.*—Length: 7.5 cm. Diameter: 0.3 cm. Color: Upper side: RHS 144B (green). Lower side: RHS 144C (green).

*Aspect.*—Petioles are mostly horizontally-directed, while the leaf blades slant downwards.

Inflorescence:

*Whole inflorescence with surrounding bracts.*—Medium to large sized, with the bracts horizontally-directed, the center is a relatively small cyme surrounded by a garland of somewhat undulated bracts.

*Diameter.*—21–23 cm.

*Height of inflorescence.*—4 cm.

Bracts:

*Description.*—Bract blade is not flat, but is moderately undulated and distinctly folded along the midrib giving a v-shaped sectional view.

*Number of bracts per inflorescence.*—11–13.

*Shape.*—Ovate.

*Base.*—Rounded to acute.

*Apex.*—Acuminate.

*Lobes.*—Weak.

*Size.*—Length: 12.5 cm. Width: 8.5 cm.

*Texture.*—Moderately rugose or rippled.

*Vein color.*—Upper surface: Corresponds closely to the bract color. Lower surface: RHS 144C (green).

*Bract color.*—Upper surface: RHS 24C to RHS 24D (salmon-orange) with RHS 37B (pink) margins; whole surface with tiny RHS 52B (pink) freckles. Lower surface: RHS 24D with small spots of RHS 50C.

*Petiole.*—Length: 0.15–0.20 cm. Color: Upper surface: RHS 37B. Lower surface: RHS 144C (green).

Cyme:

*Cyme.*—Diameter: 0.28–0.33 cm.

*Cyathia number.*—10 borne in a cluster.

*Cyathium.*—Shape: Ovate. Diameter: 0.5–0.6 cm. Color: RHS 144B (green), top is RHS 29C (orange).

*Peduncle.*—Color: RHS 143C (green). Length: 0.4 cm.

*Nectar cups.*—Number: One per cyathium. Size: 0.5–0.6 cm wide. Color: RHS 13A (yellow).

Reproductive organs:

*Stamens.*—Number: 10–20 in a cluster. Filaments: Length: 0.2–0.3 cm. Color: RHS 29C (orange). Pollen: Quantity: Moderate. Color: RHS 12A (yellow).

Disease and insect resistance: No observations made.

COMPARISON WITH KNOWN CULTIVARS

The most similar cultivars in comparison to 'Fiscinne' are the parental cultivar 'Fismille' (U.S. Plant Pat. No. 13,660), the variety 'Fisvinci' (U.S. Plant Pat. No. 14,107), and the cultivar 'Fiscor Candy' (U.S. Plant Pat. No. 11,593). In comparison to 'Fismille', 'Fiscinne' has a different bract color, is shorter in height and has leaves which show distinct lobes.

In comparison to 'Fisvinci', 'Fiscinne' has a lighter, more yellow-orange, less pink main hue of bract color and develops less distinct lobing of bracts and leaves. Additionally, 'Fiscinne' has a taller and more upright plant habit.

In comparison to 'Fiscor Candy', 'Fiscinne' has a much earlier flowering response, its bracts are not flat, but undulated, and its plant habit is less wide with the branches more upright-directed.

I claim:

1. A new and distinct cultivar of Poinsettia plant as shown and described herein.

* * * * *